United States Patent
Setsuda et al.

(10) Patent No.: US 10,481,082 B2
(45) Date of Patent: Nov. 19, 2019

(54) MEASURING DEVICE

(71) Applicant: YOKOGAWA ELECTRIC CORPORATION, Tokyo (JP)

(72) Inventors: Kazuki Setsuda, Tokyo (JP); Naomichi Chida, Tokyo (JP)

(73) Assignee: YOKOGAWA ELECTRIC CORPORATION, Tokyo (JP)

(*) Notice: Subject to any disclaimer, the term of this patent is extended or adjusted under 35 U.S.C. 154(b) by 0 days.

(21) Appl. No.: 16/026,759

(22) Filed: Jul. 3, 2018

(65) Prior Publication Data

US 2019/0011353 A1  Jan. 10, 2019

(30) Foreign Application Priority Data

Jul. 6, 2017 (JP) .................................. 2017-132960

(51) Int. Cl.
   *G01N 21/86* (2006.01)
   *G01N 21/25* (2006.01)
   *G01N 21/3559* (2014.01)
   *G01N 21/31* (2006.01)
   (Continued)

(52) U.S. Cl.
   CPC ....... *G01N 21/255* (2013.01); *G01N 21/3103* (2013.01); *G01N 21/3559* (2013.01); *G01N 21/86* (2013.01); *G01N 33/346* (2013.01); *G01N 33/442* (2013.01); *G01N 2021/3148* (2013.01); *G01N 2021/869* (2013.01); *G01N 2021/8636* (2013.01); *G01N 2021/8663* (2013.01); *G01N 2201/061* (2013.01)

(58) Field of Classification Search
   CPC .... G01N 21/255; G01N 21/31; G01N 21/532; G01N 33/343
   See application file for complete search history.

(56) References Cited

U.S. PATENT DOCUMENTS

| | | | | |
|---|---|---|---|---|
| 7,961,305 B2* | 6/2011 | Xu | ........................ | A61B 5/1455 356/39 |
| 2012/0218542 A1* | 8/2012 | Ichizawa | ............ | G01N 21/3554 356/51 |
| 2017/0000394 A1* | 1/2017 | Al-Ali | .................. | A61B 5/7278 |

FOREIGN PATENT DOCUMENTS

| CN | 1800825 A | 7/2006 |
|---|---|---|
| JP | 2012-173249 A | 9/2012 |
| JP | 2016-095258 A | 5/2016 |

OTHER PUBLICATIONS

Colette A. Sacksteder, "A portable, non-focusing optics spectrophotometer (NoFOSpec) for measurements of steady-state absorbance changes in intact plants", Jun. 2001, Kluwer asdemic Publishers (Year: 2001).*

(Continued)

*Primary Examiner* — Maurice C Smith
(74) *Attorney, Agent, or Firm* — Osha Liang LLP (57) ABSTRACT

A measuring device includes: an irradiator that irradiates electromagnetic waves to an inspection object; a light collector having a reflecting surface that guides, to a light-collecting surface, electromagnetic waves whose incident angle with respect to an incident end facing the inspection object is within a predetermined angle, among the electromagnetic waves that have been transmitted through the inspection object; and a detector that detects the electromagnetic waves guided to the light-collecting surface. The measuring device measures a characteristic of the inspection object based on the detected electromagnetic waves.

17 Claims, 6 Drawing Sheets

(51) Int. Cl.
    *G01N 33/34*     (2006.01)
    *G01N 33/44*     (2006.01)

(56) References Cited

OTHER PUBLICATIONS

R. B. Miles,"Hennispherical-field-of-view, nonimaging narrow-band spectral filter", Jul. 24, 1981 Optics Letters (Year: 1981).*
Joseph P. Rice, "Spatial uniformity comparison of two noninnaging concentrators",(Novennber 1997)Opt. Eng. 36(11) 2943-2947.*
Welford, W. T. et al., "Nonimaging Concentrators: The Compound Parabolic Concentrator" High Collection Nonimaging Optics, Elsevier Science & Technology, XP055500414, p. 53-76 (24 pages).

* cited by examiner

MEASURING DEVICE

BACKGROUND

Technical Fields

The present invention relates to a measuring device, for example, a measuring device for measuring characteristics of a sheet-like measurement object such as paper.

Related Art

Measurement and control of the amount of moisture is extremely important in paper manufacturing processes. Paper is traded by weight. However, the weight varies depending on the amount of moisture and thus the amount of moisture at the time of weighing is strictly controlled. Therefore, moisture measuring sensors for monitoring the amount of moisture in paper are required in papermaking processes. General techniques employed in the method of measuring the amount of moisture include, for example, a technique of calculating the amount of moisture by performing multivariate analysis on an absorbance measured using near-infrared rays and a technique of measuring the amount of moisture based on the resonance frequency of microwaves.

Figure 1:
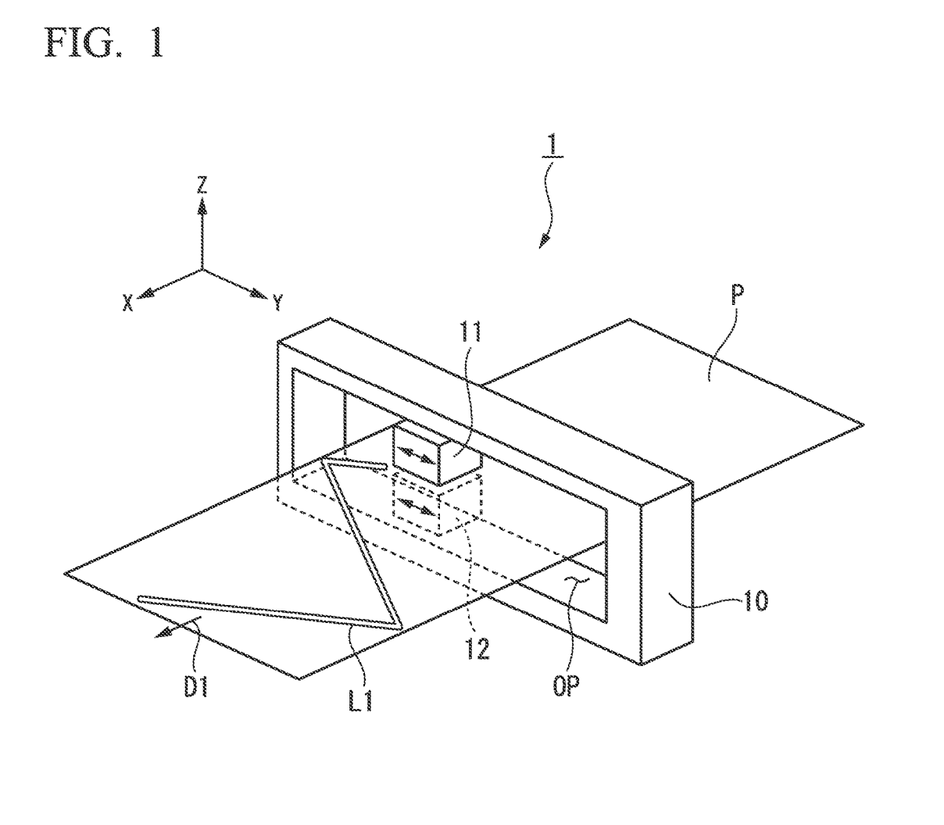
FIG. 1 is a perspective view showing a schematic configuration of a measuring device according to one or more embodiments of the present invention.

In the related art, an infrared absorption moisture meter has been proposed as a measuring device that calculates the amount of moisture based on an absorbance measured using near-infrared rays. As shown in FIG. 1, the infrared absorption moisture meter includes a frame 10 (an O-shaped frame), an upper sensor head 11, and a lower sensor head 12. The upper sensor head 11 and the lower sensor head 12 engage with the frame 10 and are reciprocally driven in the Y direction in synchronization with each other such that the upper sensor head 11 and the lower sensor head 12 are located at the same position in the Y direction. A conveyance mechanism conveys paper P as a measurement object in a contactless manner between the upper sensor head 11 and the lower sensor head 12 in the direction from the back to the front of the drawing.

Figure 5:
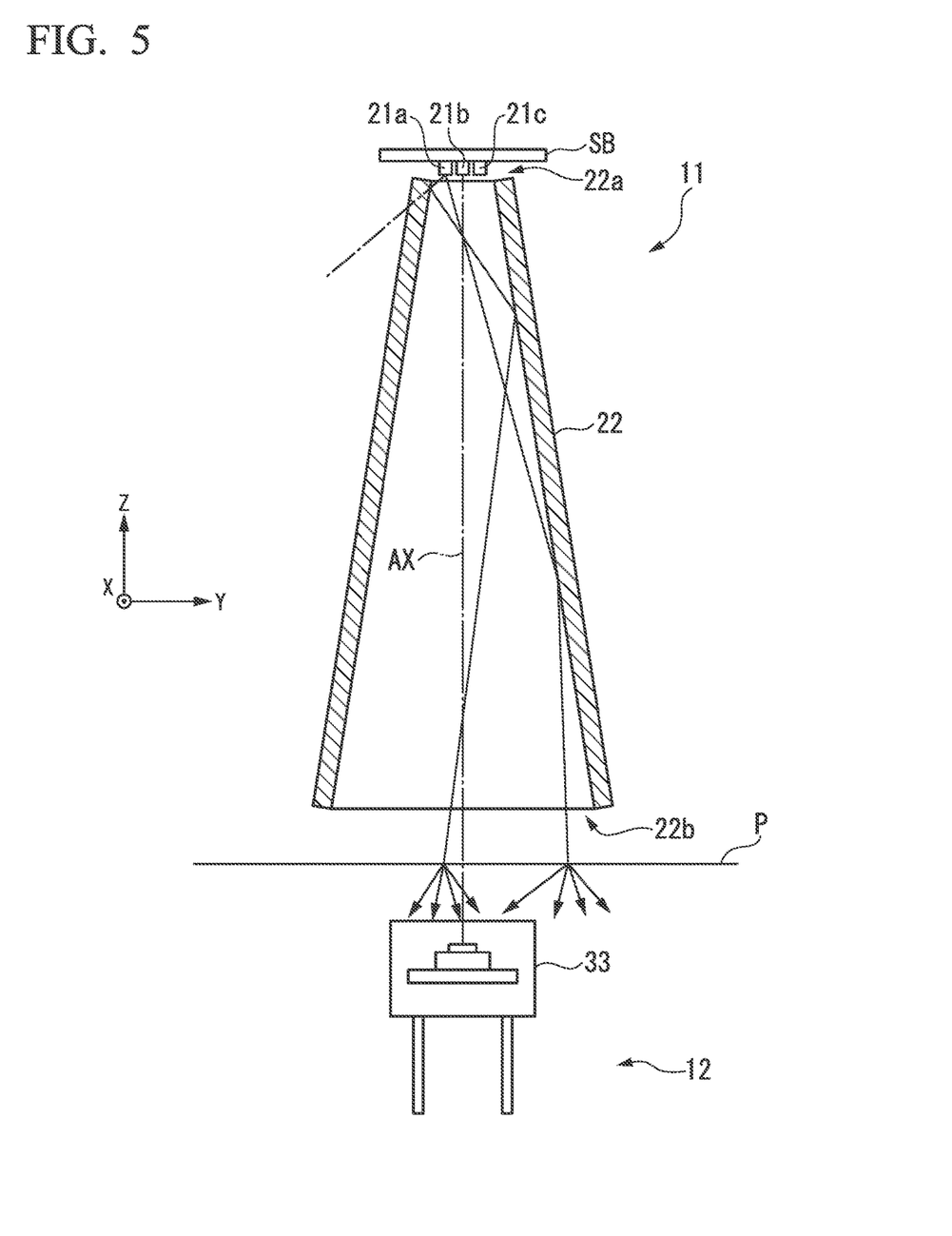
FIG. 5 is a front perspective view showing the internal configuration of an upper sensor head and a lower sensor head of a measuring device of the related art.

In the infrared absorption moisture meter, upper components are provided on the upper sensor head 11 and lower components are provided on the lower sensor head 12 with the paper P interposed therebetween as shown in FIG. 5. For example, a light source and an inner-surface reflecting mirror 22 (a light pipe) are provided as the upper components and a detector 33 which is a light receiver is provided as a lower component.

The light source includes a substrate SB on which light emitting elements 21a to 21c that irradiate a light of a wavelength $\lambda 1$ of 1.94 μm which is absorbed to a great extent by water, a light of a wavelength $\mu 2$ of 2.1 μm which is absorbed to a great extent by cellulose which is a major part of the raw material of paper, and a light of a wavelength $\lambda 3$ of 1.7 μm which is not absorbed by any of water and cellulose, respectively, are arranged. For example, a printed circuit board or a ceramic substrate is used as the substrate SB. The light emitting elements are brought as close as possible to an incident end 22a of the inner-surface reflecting mirror. The inner-surface reflecting mirror 22 has a pyramidal shape and reflects infrared rays irradiated from the light source in a direction toward the paper. Accordingly, the infrared rays irradiated from the light source are transmitted through the paper P and the detector 33 receives the infrared rays transmitted through the paper. To calculate the amount of moisture, the detector 33 measures the absorbances of infrared rays having the wavelengths $\lambda 1$ to $\lambda 3$ as follows.

Paper P which is a measurement object is placed at an interval of several millimeters from the bottom of the inner-surface reflecting mirror 22. Below the paper P, the detector 33 is arranged almost on the optical axis AX of the inner-surface reflecting mirror at an additional interval of several millimeters from the paper P. The detector 33 receives a light flux emitted from an exit end 22b of the inner-surface reflecting mirror 22 and obtains a transmission attenuation factor of each wavelength by using a detection circuit (not shown) and a calculation processor (not shown). For example, the calculation processor determines the transmission attenuation factor of water from the intensity of the wavelengths $\lambda 1$ and the intensity of the wavelength $\lambda 3$ and measures the amount of moisture based on the determined transmission attenuation factor. The light sources of wavelengths $\lambda 1$, $\mu 2$, and $\lambda 3$ are modulated and lit at different frequencies, and thus the respective intensities of the wavelengths for the signals detected by the detector 33 are distinguished by frequency. Further, the calculation processor determines the transmission attenuation factor of cellulose from the intensity of the wavelength $\mu 2$ and the intensity of the wavelength $\lambda 3$ and measures the amount of cellulose which is a major part of the composition of paper based on the determined transmission attenuation factor. The calculation processor calculates the proportion of moisture by dividing the amount of moisture by the amount of cellulose. The infrared absorption moisture meter can measure the proportion of moisture from the ratio between the amount of cellulose and the amount of moisture using a single sensor as described above. The infrared absorption moisture meter is most popular as a paper moisture meter since it has a high measurement resolution.

Figure 6:
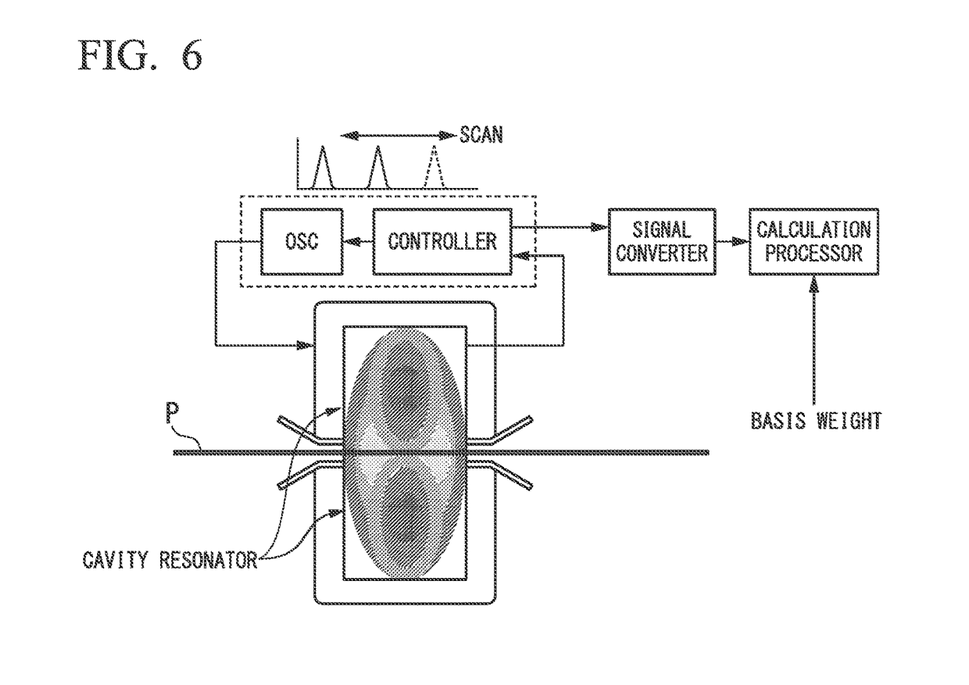
FIG. 6 is a schematic block diagram showing a configuration of a cavity resonance type moisture meter of the related art.

FIG. 6 is a schematic block diagram showing another example of the measuring device. The measuring device shown in FIG. 6 is a microwave moisture meter that measures the amount of moisture based on the resonance frequency of microwaves. Components above paper P which is a measurement object are provided on an upper sensor head and components below the paper P are provided on a lower sensor head. The microwave moisture meter has a cavity resonator having a cavity divided into upper and lower parts with the paper interposed therebetween. The microwave moisture meter has an oscillator (OSC) for resonating microwaves in this cavity. The oscillator scans frequencies of oscillating microwaves by a controller and a signal converter converts a frequency at which the impedance of the cavity resonator is maximized into a voltage and outputs the voltage. The resonance frequency varies depending on a dielectric material (the amount of moisture contained in the paper) interposed within the cavity resonator. The calculation processor can determine the amount of moisture corresponding to the measured resonance frequency with reference to a known relationship between the resonance frequency and the amount of moisture. Then, the amount of moisture is calculated using a basis weight signal from a basis weight sensor (not shown).

In the infrared absorption moisture meter of the related art, the intensity of light arriving at the light receiver is significantly lowered for thick paper (with a high basis weight) containing a large amount of fibers, carbon or the like due to the influence of diffusion by fibers of the paper or the influence of additives such as carbon when the paper contains such additives. As a unit of paper thickness, the basis weight indicates the weight of paper per square meter.

Therefore, the infrared absorption moisture meter of the related art sometimes fails to measure the transmission attenuation factor and also the amount or proportion of moisture. A microwave moisture meter may be used to measure such thick paper. However, a basis weight meter is required separately to measure the proportion of moisture since the microwave moisture meter can measure only the amount of moisture. In addition, the microwave moisture meter tends to have an increase measurement error because the proportion of moisture is determined based on the resonance frequency. Further, the microwave moisture meter requires temperature compensation to reduce the influence of paper temperature, lacks the ability to measure local changes in the amount of moisture since the cross section of the resonator through which the paper P passes is large, and is expensive since the device configuration is complicated. Therefore, it was expected that the infrared absorption moisture meter would have been utilized as much as possible in measurement of the amount or proportion of moisture.

SUMMARY

A measuring device in accordance with one or more embodiments of the invention measures a characteristic of an inspection object based on a detection result of electromagnetic waves which have been transmitted through the inspection object. The measuring device includes an irradiator configured to irradiate electromagnetic waves to the inspection object, a light collector having a reflecting surface which guides, to a light-collecting surface, electromagnetic waves whose incident angle with respect to an incident end facing the inspection object is within a predetermined incident angle, among the electromagnetic waves which have been transmitted through the inspection object, and a detector configured to detect the electromagnetic waves guided to the light-collecting surface.

Further features and aspects of the present disclosure will become apparent from the following detailed description of exemplary embodiments with reference to the attached drawings.

DETAILED DESCRIPTION

The present invention will be now described herein with reference to illustrative embodiments. Those skilled in the art will recognize that many alternative embodiments can be accomplished using the teaching of the present invention and that the present invention is not limited to the embodiments illustrated herein for explanatory purposes.

One or more embodiments of the present invention provide a measuring device which can increase the range of measurable thicknesses of measurement objects.

Hereinafter, embodiments of a measuring device according to the present invention will be described with reference to the drawings. For ease of understanding, the following description will be given with regard to an example in which the measuring device according to one or more embodiments is mainly applied to an infrared absorption moisture meter which is a type of infrared ray analyzer. One or more embodiments can also be applied to devices for measuring other measurement objects such as a basis weight meter (a paper thickness gauge).

FIG. 1 is a perspective view showing a schematic configuration of a measuring device 1 according to one or more embodiments of the present invention. As shown in FIG. 1, the measuring device 1 includes a frame 10 (an O-shaped frame), an upper sensor head 11 (a first head), and a lower sensor head 12 (a second head). For example, the measuring device 1 is attached to a paper machine installed in a paper mill and measures the fraction of moisture contained in paper P (an inspection object) manufactured by the paper machine.

The positional relationship between each member will sometimes be described with reference to an XYZ orthogonal coordinate system set in each figure. However, for convenience of explanation, the origins of the XYZ orthogonal coordinate systems shown in the figures are not the same and their positions may be different in the figures. In the XYZ orthogonal coordinate system shown in FIG. 1, the X axis is set in a direction along the conveying direction D1 of the paper P, the Y axis is set in the width direction of the paper P, and the Z axis is set in the vertical direction.

The frame 10 is a member having a substantially rectangular ring shape whose external shape has a long-side direction and a short-side direction. The frame 10 supports the upper sensor head 11 and the lower sensor head 12 such that the upper sensor head 11 and the lower sensor head 12 can reciprocate in the long-side direction within an opening portion OP of the frame 10. Specifically, the long-side direction of the frame 10 is set in a direction along the width direction (Y direction) of the paper P, the short-side direction of the frame 10 is set in a direction along the vertical direction (Z direction), and the frame 10 is arranged such that the paper P passes through almost the center of the opening portion OP.

That is, the frame 10 is positioned with respect to the paper P such that the upper sensor head 11 is disposed above the paper P being conveyed while the lower sensor head 12 is disposed below the paper P being conveyed. Although not shown in FIG. 1, the frame 10 has a mechanism for reciprocating the upper sensor head 11 in the long-side direction along the front surface of the paper P and a mechanism for reciprocating the lower sensor head 12 in the long-side direction along the back surface of the paper P. By driving these mechanisms in the same way, it is possible to synchronously reciprocate the upper sensor head 11 and the lower sensor head 12.

The upper sensor head 11 is supported by the frame 10 such that the upper sensor head 11 can reciprocate in the width direction of the paper P along the front surface of the paper P as described above. The upper sensor head 11 irradiates a plurality of infrared light beams (near-infrared light beams) having different wavelengths toward the front surface of the paper P. Specifically, a near-infrared light beam having a wavelength λ1 (for example, 1.94 µm) at which the absorptivity of water is higher than the absorptivity of cellulose, a near-infrared light beam having a wavelength µ2 (for example, 2.1 µm) at which the absorptivity of cellulose which is a major component of paper is higher than the absorptivity of water, and a near-infrared light beam having a wavelength µ3 (for example, 1.7 µm) at which the absorptivities of water and cellulose are lower than those of the wavelengths λ1 and µ2 are irradiated onto the front surface of the paper P.

The lower sensor head 12 is supported by the frame 10 such that the lower sensor head 12 can reciprocate in the width direction of the paper P along the back surface of the paper P as described above, and receives near-infrared light transmitted through the paper P. Moisture contained in the paper P is measured based on a detection result of the near-infrared light received by the lower sensor head 12. The lower sensor head 12 reciprocates in the width direction (Y direction) of the paper P in synchronization with the upper sensor head 11 with the paper P being conveyed in the conveying direction D1 (X direction) therebetween and therefore the amount of moisture contained in the paper P is measured along a zigzag-like measurement line L1 shown in FIG. 1.

Figure 2:
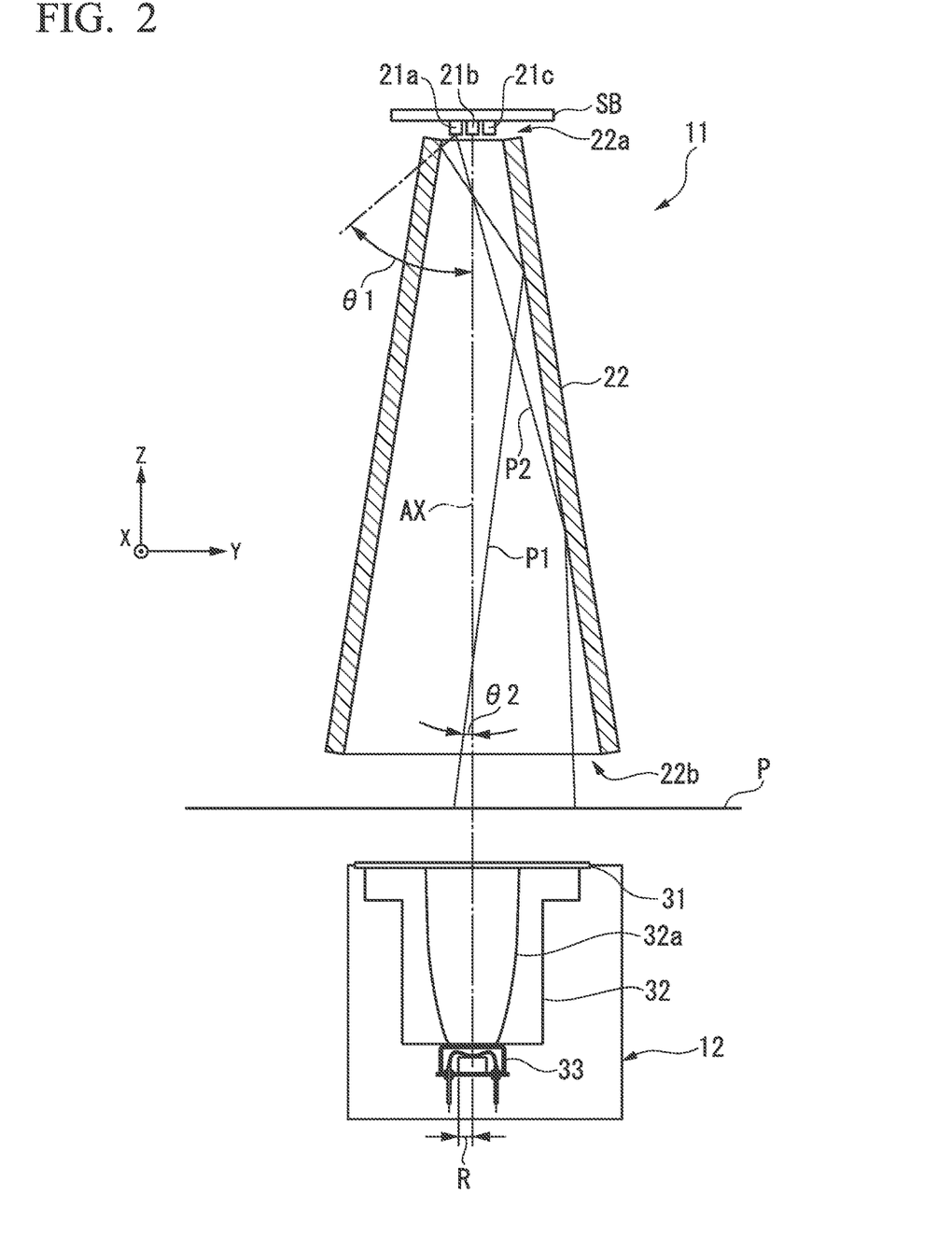
FIG. 2 is a front perspective view showing internal configurations of an upper sensor head and a lower sensor head of the measuring device according to one or more embodiments of the present invention.

Next, internal configurations of the upper sensor head 11 and the lower sensor head 12 will be described. FIG. 2 is a front perspective view showing the internal configurations of the upper sensor head 11 and the lower sensor head 12 of the measuring device 1. Illustration of casings of the upper sensor head 11 and the lower sensor head 12 is omitted in FIG. 2. The upper sensor head 11 is shown partially in cross-section. As shown in FIG. 2, the upper sensor head 11 includes an inner-surface reflecting mirror 22 (a light pipe) and light emitting elements 21a to 21c as light sources constituting an irradiator for irradiating electromagnetic waves.

The light emitting elements 21a to 21c emit near-infrared light which is to be irradiated onto the front surface of the paper P. The light emitting elements 21a to 21c are, for example, semiconductor light emitting elements such as laser diodes (LDs) or light emitting diode (LEDs). Specifically, the light emitting element 21a emits near-infrared light having a wavelength λ1 (for example, 1.94 µm) at which the absorptivity of water is sufficiently higher than the absorptivity of cellulose. The light emitting element 21b emits near-infrared light having a wavelength µ2 (for example, 2.1 µm) at which the absorptivity of cellulose is sufficiently higher than the absorptivity of water. The light emitting element 21c emits near-infrared light having a wavelength λ3 (for example, 1.7 µm) at which the absorptivities of water and cellulose are sufficiently lower than those of the wavelengths λ1 and λ2. The light emitting elements 21a to 21c are arranged in a linear or planar form at regular intervals on a plate-shaped substrate SB such as a printed circuit board or a ceramic substrate.

The inner-surface reflecting mirror 22 is a polygonal optical element which is disposed between the light emitting elements 21a to 21c and the paper P and reflects near-infrared light emitted from the light emitting elements 21a to 21c multiple times to achieve a uniform intensity distribution. Specifically, the inner-surface reflecting mirror 22 has an incident end 22a which is quadrangular in shape in the XY plane and through which near-infrared light emitted from the light emitting elements 21a to 21c enters the inner-surface reflecting mirror 22, and an exit end 22b which is similar in shape to the incident end 22a in the XY plane and from which the multiple-reflected near-infrared light is emitted. The inner-surface reflecting mirror 22 also has a tapered shape such that the exit end 22b is formed to be larger than the incident end 22a.

Specifically, the length of one side of the incident end 22a of the inner-surface reflecting mirror 22 is set to, for example, about several millimeters and the length of one side of the exit end 22b is set to, for example, about ten to several tens of millimeters. Here, the spot diameter of near-infrared light emitted from the inner-surface reflecting mirror 22 is set to be about equal in size to a measurement region set on the paper P and is defined according to the size of the exit end 22b. Therefore, the size of the exit end 22b is set to be about equal to that of the measurement region set on the paper P. The inner-surface reflecting mirror 22 is disposed between the light emitting elements 21a to 21c and the paper P such that the light emitting elements 21a to 21c mounted on the substrate SB are as close to the incident end 22a as possible and the distance between the inner-surface reflecting mirror 22 and the front surface of the paper P is about several millimeters.

Here, near-infrared light beams which are emitted from the light emitting element 21a disposed at a position deviated from an optical axis AX defined along the central axis of the inner-surface reflecting mirror 22 and then pass through paths P1 and P2 will be considered. The near-infrared light beam passing through the path P1 is emitted from the light emitting element 21a at an angle of θ1 with respect to the optical axis AX and enters the inner-surface reflecting mirror 22 through the incident end 22a. Each time the near-infrared light beam passing through the path P1 is reflected twice on an inner surface of the inner-surface reflecting mirror 22, the angle of the beam with respect to the optical axis AX gradually decreases and finally reaches θ2 (θ1>θ2) when the beam is emitted from the exit end 22b. Similarly, the near-infrared light beam passing through the path P2 is reflected once by the inner surface of the inner-surface reflecting mirror 22, such that the beam is emitted from the exit end 22b at a small angle with respect to the optical axis AX.

As described above, the near-infrared light beam which has entered the inner-surface reflecting mirror 22 through the incident end 22a is reflected (multiple-reflected) inside the inner-surface reflecting mirror 22, whereby the angle of the beam with respect to the optical axis AX gradually decreases and the beam is emitted from the exit end 22b at a decreased angle. Therefore, even if the angles of near-infrared light beams with respect to the optical axis AX when incident on the incident end 22a (i.e., the angles of the near-infrared light beams when emitted from the light emitting elements 21a to 21c) differ from each other, near-infrared light beams which are substantially parallel to the optical axis AX exit the inner-surface reflecting mirror 22. Thus, the front surface of the paper P is irradiated with near-infrared light having a uniform intensity distribution with a spot diameter not greater than necessary.

On the other hand, the lower sensor head 12 includes a protection window 31, a light collector 32, and a detector 33 as shown in FIG. 2.

The protection window 31 is made of a substance which prevents adhesion of the paper P and other objects to the light collector 32 and transmits near-infrared light emitted from the light emitting elements 21a to 21c. Such a substance is, for example, a silicate (glass).

The light collector 32 has an opening portion, and near-infrared light transmitted through the protection window 31 after being emitted from the back surface of the paper P is incident on the front side of the opening portion as an incident end 32b. The front side and the back side of the opening portion indicate a side thereof facing the paper P and a side facing the detector 33, respectively, among the main sides of the opening portion. The light collector 32 collects the incident near-infrared light, guides the near-infrared light whose incident angle is within a predetermined incident angle to the back side of the opening portion as an exit end 32c, and emits the near-infrared light guided to the exit end 32c to the detector 33. The light collector 32 is made of a mechanically stable material such as metal or glass and a reflecting surface 32a is formed on the inner surface of the light collector 32. The reflecting surface 32a is coated with a substance, such as gold, having a sufficiently high reflectance for incident near-infrared light. A more detailed configuration of the light collector 32 will be described later.

The detector 33 has a light receiving surface positioned on an extension line of the optical axis AX and is disposed below the paper P such that the distance between the light receiving surface and the exit end 32c of the light collector 32 facing it is equal to or less than several millimeters. Thus, the detector 33 detects near-infrared light obtained via the paper P and the light collector 32 (the near-infrared light incident on the front surface of the paper P and transmitted through the back side of the paper P). For example, a PbS element, a Ge element, or an InGaAs element can be used as the light receiving element of the detector 33.

Here, the PbS element is a photoconductive element containing lead sulfide as a main component and enables detection of light in a wavelength region of about 0.6 to 3.0 µm. The detection sensitivity of the PbS element is maximized at around a wavelength of 2.0 µm. The Ge element is a photoconductive element containing germanium as a main component. The Ge element can detect light in a wavelength range of about 0.6 to 1.8 µm. The InGaAs element is a ternary mixed crystal semiconductor element containing indium, gallium, and arsenic as main components. The InGaAs element enables detection of light in a wavelength range of about 0.9 to 2.3 µm and the detection sensitivity is maximized at around wavelengths of 1.5 to 1.8 µm.

Figure 3:
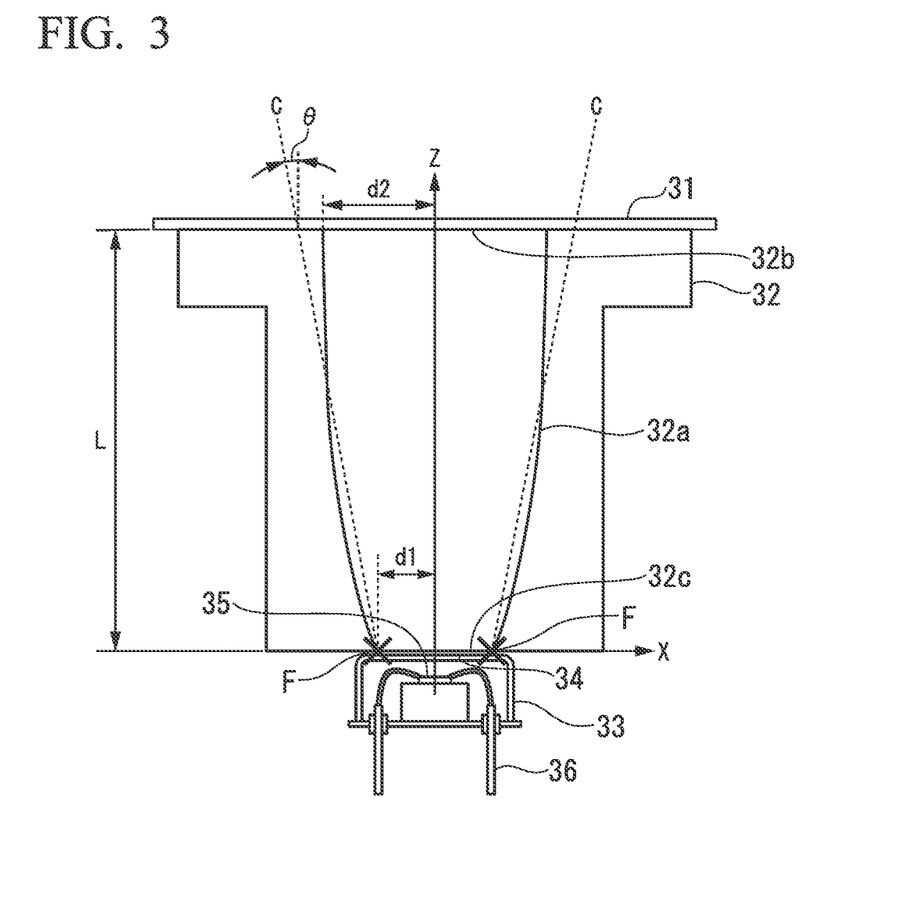
FIG. 3 is a front perspective view showing the internal configuration of the lower sensor head of the measuring device according to one or more embodiments of the present invention.

Next, the internal configuration of the lower sensor head 12 will be described in more detail. FIG. 3 is a front perspective view showing the internal configuration of the lower sensor head 12.

In the example shown in FIG. 3, the light collector 32 is a compound parabolic concentrator (CPC) having an opening portion which passes therethrough from the front side to the back side thereof. The shape of the reflecting surface 32a formed on the inner side of the opening portion is a compound paraboloidal surface. The reflecting surface 32a is rotationally symmetric about the Z axis as a rotation axis. A curve where the reflecting surface 32a and a cross section passing through the Z axis intersect is a parabola. The relationship between X and Z coordinates on the parabola where the reflecting surface 32a and a cross section passing through the rotation axis and parallel to the X axis intersect is expressed by formula (1).

$$x = a + b(c + d \cdot z)^{1/2} + e \cdot z \quad (1)$$

A broken line C represents the axis of the parabola and the angle θ represents the angle between the axis C and the Z axis. The incident end 32b formed on the front side of the opening portion and the exit end 32c formed on the back side of the opening portion are shaped as concentric circles centered on the Z axis and the radius d2 of the incident end 32b is greater than the radius d1 of the exit end 32c. A focal point F of the reflecting surface 32a is formed on the periphery of the exit end 32c. With such a configuration, of the components of light incident on the incident end 32b through the protection window 31 disposed on the front surface of the light collector 32, light components reflected from the reflecting surface 32a whose incident angles are smaller than the angle θ are emitted from the exit end 32c. That is, the angle θ is an angle for allowing the reflected light to be emitted from the exit end 32c. This angle θ is referred to as an allowable acceptance angle. Therefore, the thickness L of the light collector 32 is (d1+d2) cot θ. When a, b, c, d, and e in formula (1) are −6.8, 8.6, 1.9, 0.25 and −0.32 respectively, θ is 45 degrees.

The detector 33 includes a window member 34, a light receiving element 35, and a lead wire 36.

The window member 34 is made of a substance which covers the periphery of the light receiving element 35 and transmits near-infrared light emitted from the exit end 32c. This prevents the adhesion of other objects to the light receiving element 35.

The light receiving element 35 receives near-infrared light emitted from the exit end 32c and transmitted through the window member 34. The light receiving element 35 is provided at a position where the front surface (light receiving surface) thereof is perpendicular to the optical axis AX and the center thereof is on an extension line of the optical axis AX. Since the area of the opening of the incident end 32b is larger than the area of the opening of the exit end 32c, the area of the opening of the incident end 32b is larger than an irradiation area of the light receiving element 35 where the light receiving element 35 is irradiated with the near-infrared light. Therefore, the intensity of near-infrared light with which the light receiving element 35 is irradiated is higher than when the light is received without passing through the light collector 32.

The light receiving element 35 generates a voltage corresponding to the intensity of the received light and has the lead wire 36 for extracting a detection signal having the generated voltage. The intensity of the light arriving at the light receiving element 35 is detected by a change in current, voltage or resistance of the extracted electric signal.

Next, the operation of the measuring device 1 configured as described above will be described. When the operation of the measuring device 1 starts, the upper sensor head 11 and the lower sensor head 12 are driven by a driving mechanism (not shown) provided in the frame 10. The upper sensor head 11 and the lower sensor head 12 synchronously reciprocate in the width direction (Y direction) of the paper P. At the same time as the driving of the upper sensor head 11 and the lower sensor head 12 starts, the driving of the light emitting elements 21a to 21c provided in the upper sensor head 11 also starts. Thereby, near-infrared light of wavelength λ1 (for example, 1.94 µm) is emitted from the light emitting element 21a, near-infrared light of wavelength µ2 (for example, 2.1 µm) is emitted from the light emitting element 21b, and near-infrared light of wavelength µ3 (For example, 1.7 µm) is emitted from the light emitting element 21c.

The each of the light emitting elements 21a to 21c emits the near-infrared light with their intensities modulated at different frequencies.

The near-infrared light emitted from the light emitting elements 21a to 21c enters the inner-surface reflecting mirror 22 through the incident end 22a and is reflected within the inner-surface reflecting mirror 22 multiple times, gradually decreasing the angle formed between the optical axis AX and the incident direction. Therefore, the near-infrared light is made uniform in intensity distribution inside the inner-surface reflecting mirror 22 and is then irradiated onto the front surface of the paper P through the exit end 22b. Some components of the near-infrared light irradiated onto the front surface of the paper P are reflected or scattered by the front surface of the paper P and the remaining components thereof pass through the paper P.

The near-infrared light transmitted through the paper P is incident on the incident end 32b of the light collector 32 via the protection window 31. Of the components of the near-infrared light incident on the incident end 32b, those having a smaller incident angle θ than the maximum incident angle are collected by the reflecting surface 32a and emitted from the exit end 32c. The light receiving element 35 is irradiated with the near-infrared light emitted from the exit end 32c via the window member 34. Thus, the intensity of the near-infrared light with which the light receiving element 35 is irradiated is made observable. A part of the near-infrared light emitted from the exit end 32c is not irradiated onto the light receiving element 35 because there is a gap between the exit end 32c and the light receiving element 35, but the proportion of the part is negligible.

The measuring device 1 further includes a detection circuit (not shown) and a calculation processor (not shown). The detection circuit separates the detection signal input from the light receiving element 35 according to the wavelength components of the near-infrared light after amplification to generate measurement signals S1, S2, and S3 corresponding to the near-infrared light of wavelengths $\lambda 1$, $\mu 2$, and $\lambda 3$ and detects the respective strengths of the measurement signals. The detection circuit notifies the calculation processor of the strengths of the detected measurement signals S1, S2, and S3. Since the light emitting elements 21a to 21c are lit with their intensities modulated at different frequencies, the detection circuit can detect the signal components of the respective wavelengths by distinguishing the signals detected by the light receiving element 35 by frequency.

The calculation processor calculates the absorptivity of the paper P at the near-infrared light by performing multivariate analysis on the strength ratios between the measurement signals S1, S2, and S3 and the absorptivity of each wavelength component.

As described above, most of the near-infrared light having the wavelength $\lambda 1$ is absorbed by water contained in the paper P when passing through the paper P and most of the near-infrared light having the wavelength $\mu 2$ is absorbed by cellulose which is a component of the paper P when passing through the paper P. On the contrary, near-infrared light of the wavelength $\lambda 3$ is less absorbed by the paper P and water contained in the paper P. Therefore, the intensities of the near-infrared light of the wavelengths $\lambda 1$ and $\mu 2$ transmitted through the paper P are smaller than the intensity of the near-infrared light of the wavelength $\lambda 3$.

Utilizing such characteristics, the calculation processor calculates, for example, the transmission attenuation factor of the wavelength $\lambda 1$ from the intensity of near-infrared light of the wavelength $\lambda 1$ and the intensity of near-infrared light of the wavelength $\lambda 3$ and calculates the transmission attenuation factor of the wavelength $\mu 2$ from the intensity of near-infrared light of the wavelength $\mu 2$ and the intensity of near-infrared light of the wavelength $\mu 3$. The transmission attenuation factors of the wavelengths $\lambda 1$ and $\mu 2$ decrease as the amount of moisture and the amount of cellulose increase, respectively. A table showing the relationship between the transmission attenuation factor of the wavelengths $\lambda 1$ and $\mu 2$ and the amount of moisture and the amount of cellulose is preset in the calculation processor. By referring to this table, the calculation processor obtains the amount of moisture and the amount of cellulose corresponding to the calculated transmission attenuation factors of the wavelengths $\lambda 1$ and $\mu 2$. The calculation processor calculates the proportion of moisture by dividing the obtained amount of moisture by the amount of cellulose. When calculating the amount of moisture and the amount of cellulose, the calculation processor may use a preset function or the like as a method other than using the table.

In the above measurement, the upper sensor head 11 and the lower sensor head 12 continue to synchronously reciprocate in the width direction (Y direction) of the paper P with the paper P being conveyed in the conveying direction D1 (X direction) shown in FIG. 1. Accordingly, the proportion of moisture contained in the paper P is measured along the zigzag-like measurement line L1 shown in FIG. 1. In one or more embodiments, the near-infrared light transmitted through the paper P is collected on the light receiving element 35 by the light collector 32, and therefore it is possible to make the intensity of collected light greater than that of the infrared absorption moisture meter of the related art.

Figure 4:
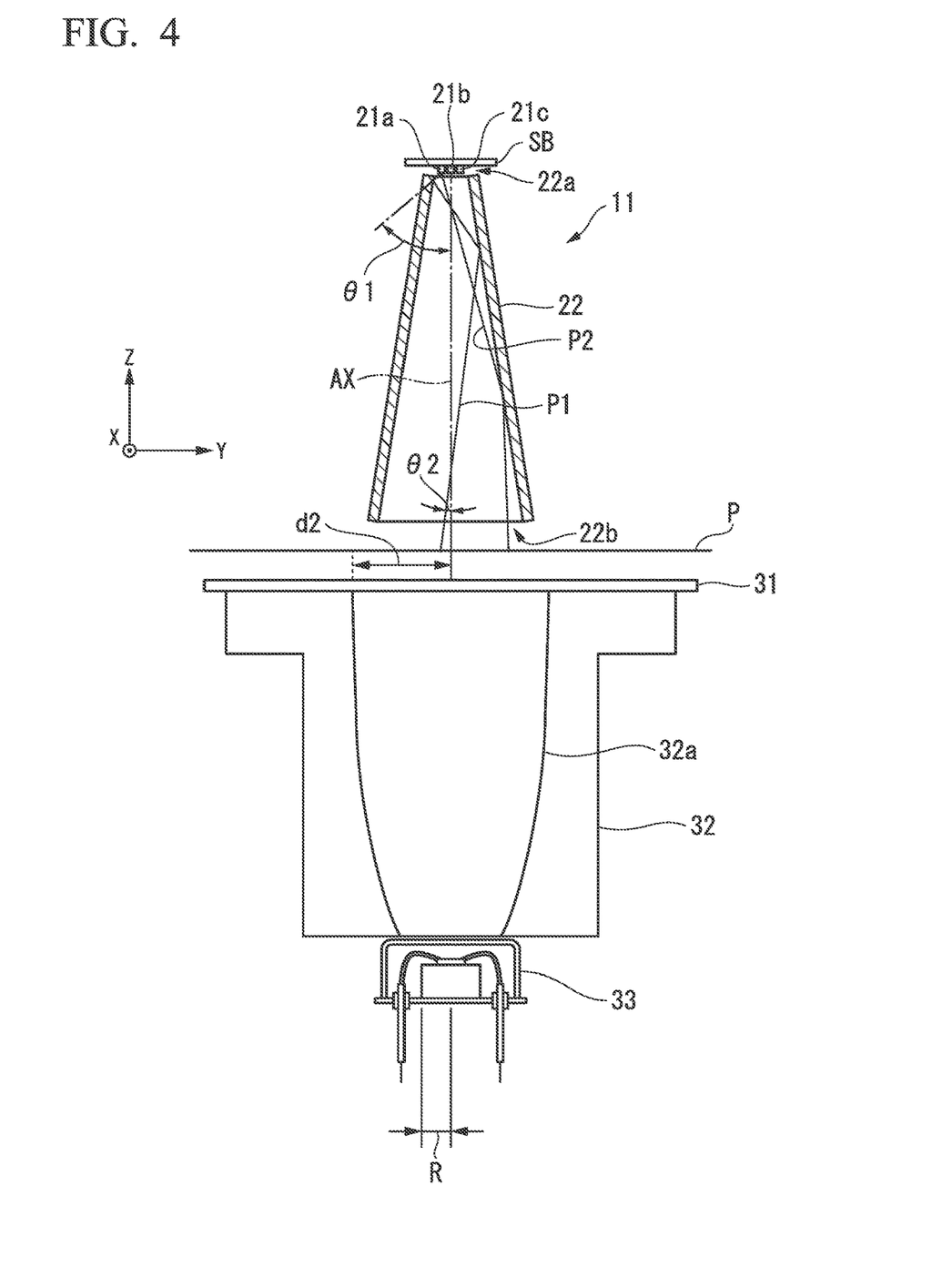
FIG. 4 is a front perspective view showing another example of the internal configurations of the upper sensor head and the lower sensor head of the measuring device according to one or more embodiments of the present invention.

For example, in the infrared absorption moisture meter of the related art shown in FIG. 4, the detector 33 is irradiated with near-infrared light transmitted through the paper P as diffused light. The perspective angle θ on the two-dimensional plane of the light receiving element of the detector 33 with respect to the paper P is expressed by the formula (2).

$$\theta = \tan^{-1}(R/L) \qquad (2)$$

In formula (2), L represents the distance from the back surface of the paper P to the surface of the light receiving element, and R represents the radius of the light receiving element. When L is 10 mm and R is 1.5 mm, θ is 8.5 degrees.

On the other hand, the light collector 32 according to one or more embodiments can collect near-infrared light of which the angle of incidence, that is, the perspective angle θ from the paper P, is within the allowable acceptance angle. The solid angle is proportional to about the square of the perspective angle θ on the two-dimensional plane. Assuming that the allowable acceptance angle of the light collector 32 is 45 degrees, the ratio of the solid angle of the light collector 32 according to one or more embodiments to the solid angle of the light receiving element of the infrared absorption moisture meter of the related art is 28 ($\approx (45/8.5)^2$). Since the intensity of light provided to the light receiving element 35 by the light collector 32 is substantially proportional to the solid angle, the sensitivity of the detector 33 in one or more embodiments increases to 28 times that of the related art. Thus, even if the paper P has a high basis weight (for example, 1000 g/m² or more) which cannot be measured by the infrared absorption moisture meter of the related art, the measuring device 1 according to one or more embodiments alone can measure the proportion of moisture without using a basis weight meter or the like. In addition, the measuring device 1 according to one or more embodiments can perform high-resolution and spatially-detailed measurement since the measurement diameter is smaller than that of the microwave moisture meter. This contributes not only to the measurement of the amount of moisture but also to the productivity in the paper manufacturing process.

As described above, the measuring device 1 according to one or more embodiments measures a characteristic of an inspection object based on a detection result of electromagnetic waves transmitted through the inspection object and includes an irradiator (for example, the light emitting elements 21a to 21c), a light collector (for example, the light collector 32), and a detector (for example, the detector 33). The irradiator is configured to irradiate electromagnetic waves to the inspection object. The light collector has a reflecting surface configured to guide electromagnetic waves, whose incident angle with respect to an incident end facing the inspection object is within a predetermined incident angle, among the electromagnetic waves transmitted through the inspection object to a specific light-collecting surface. The detector is configured to detect the electromagnetic waves guided to the light-collecting surface.

Here, the specific light-collecting surface is an opening surface in an exit end (for example, the exit end 32c) facing the detector (for example, the detector 33). The shape of the reflecting surface is a compound paraboloidal surface. An opening area of the incident end of the light collector is larger than an irradiation area where the inspection object is irradiated with electromagnetic waves. The shape of the inspection object is a sheet whose thickness is sufficiently smaller than the width and length.

With this configuration, electromagnetic waves whose incident angle with respect to the incident end is within the predetermined incident angle are guided to the light-collecting surface and therefore the intensity of electromagnetic waves attenuated by transmission through the inspection object can be made greater at the light-collecting surface than at the incident end. Therefore, it is possible to measure inspection objects with thicknesses for which the measuring device of the related art cannot measure characteristics due to the attenuation of electromagnetic waves transmitted, thus increasing the range of measurable thicknesses. Since the shape of the reflecting surface is a compound paraboloidal surface, the capturing angle of the light can be made larger in comparison with a case that the shape of the reflecting surface is an inverted truncated cone, for example. Therefore, the measuring device of one or more embodiments can collect light more than the case that the shape of the reflecting surface is an inverted truncated cone, and the measurement accuracy can be improved.

Further, the electromagnetic waves irradiated by the irradiator include a first wavelength component at which an absorptivity of a liquid (for example, water) contained in the inspection object is higher than an absorptivity of a main component (for example, cellulose) of the inspection object, a second wavelength component at which an absorptivity of the main component is higher than an absorptivity of the liquid, and a third wavelength component at which an absorptivity of the liquid is lower than that of the first wavelength component and an absorptivity of the main component is lower than that of the second wavelength component.

With this configuration, it is possible to determine the amount of the liquid in the inspection object from the intensities of the first and third wavelength components and to determine the amount of the main component in the inspection object from the intensities of the second and third wavelength components. Therefore, complicated calculations or device configurations are not required to measure the amount or proportion of such liquids or main components.

Although embodiments of the present invention have been described above with reference to the drawings, specific configurations are not limited to those described above and various design changes or the like can be made without deviating from the spirit of the present invention.

The above embodiments have been described with reference to the case in which semiconductor light sources are used as light sources of three wavelengths as an example, but the light sources are not limited to semiconductor light sources. For example, optical band transmission filters that transmit wavelengths necessary for light sources that irradiate light in a wide wavelength range such as halogen lamps may also be used.

Instead of the method of modulating and lighting the light sources at different frequencies, the light sources may emit light of their respective wavelengths at different times and the detector 33 may synchronize with the lighting time of each wavelength to detect a signal component of the wavelength.

The inspection object is not necessarily paper. For example, the inspection object may be a cloth, a plastic or another resin sheet, or other sheet-like objects such as metal foils. The characteristics of the inspection object are not limited to the amount or proportion of moisture but may be the amount or proportion of a subcomponent mixed or infiltrated into the inspection object. For example, the characteristics of the inspection object may be the amount or proportion of a liquid such as a fat or alcohol as the subcomponent. In this case, the electromagnetic waves emitted by the irradiator may include first and second wavelength components which give peak absorptivities inherent respectively to a main component of the inspection object and a subcomponent contained in the inspection object and a third wavelength component having low absorptivities for both the component and the subcomponent. For example, when measuring the amount or proportion of a fat having a peak of absorptivity at a wavelength of 6.9 μm, the electromagnetic waves emitted by the irradiator may include at least a first wavelength component of 6.9 μm, a second wavelength component having a peak absorptivity for the main component, and a third wavelength component having lower absorptivities for both the main component and the sub component. The wavelength characteristics with respect to the absorptivity vary depending on the main component of the inspection object and the subcomponent contained therein. Therefore, the electromagnetic waves emitted by the irradiator are not limited to near-infrared rays but may also be far-infrared, visible, or ultraviolet rays.

In order to further increase the intensity of electromagnetic waves with which the light receiving element 35 is irradiated, the light collector 32 may be arranged such that the measurement region set on the paper P perpendicular to the direction of the optical axis AX is included in the region of the incident end 32b of the light collector 32 as shown in FIG. 4. This can ensure that the length of the diagonal line of the exit end 22b of the inner-surface reflecting mirror 22 is equal to or smaller than the diameter (2·d2) of the incident end 32b of the light collector 32. This can reduce the rate at which the electromagnetic waves irradiated from the exit end 22b of the inner-surface reflecting mirror 22 leak without being incident on the incident end 32b of the light collector 32 via the inspection object and the protection window 31.

Further, the light receiving element 35 may be arranged such that the distance between the exit end 32c of the light collector 32 and the surface of the light receiving element 35 is made as small as possible and the region of the exit end 32c perpendicular to the direction of the optical axis AX is included in the region of the light receiving element 35.

Here, the radius d1 of the exit end 32c of the light collector 32 may be made equal to or less than the radius of the surface of the light receiving element 35. The window member 34 may also be omitted. This can suppress the rate at which electromagnetic waves emitted from the exit end 32c of the light collector 32 leak without being irradiated onto the light receiving element 35.

In addition, a convex lens may be disposed at a position between the exit end 32c of the light collector 32 and the surface of the light receiving element 35 with the optical axis of the convex lens being on the extension line of the optical axis AX. The convex lens disposed at this position converges electromagnetic waves emitted from the exit end 32c of the light collector 32 to an area on the surface of the light receiving element 35. This configuration can also reduce the rate at which electromagnetic waves emitted from the exit end 32c of the light collector 32 leak without being irradiated onto the light receiving element 35. The convex lens may be configured as a portion of the window member 34. This can avoid an increase in the number of parts.

The shape of the reflecting surface 32a of the light collector 32 is not necessarily limited to a compound paraboloidal surface and may be, for example, a normal paraboloid of revolution. In that case, the light receiving element 35 may be provided at a position where the focal point of the reflecting surface 32a is arranged on the surface of the light receiving element 35. The exit end 32c of the light collector 32 may be provided at a position where the focal point of the reflecting surface 32a is within the opening surface of the exit end 32c or may be provided at a position closer to the incident end 32b than to the focal point of the reflecting surface 32a (that is, at an upper position on the light collector 32). Also with this arrangement, electromagnetic waves incident on the incident end 32b can be led to the surface of the light receiving element 35 such that the intensity of electromagnetic waves emitted to the light receiving element 35 is made higher than the intensity of electromagnetic waves incident on the incident end 32b.

When the shape of the reflecting surface 32a is a normal paraboloid of revolution, the exit end 32c may be provided without opening a rear surface of the light collector 32. A support member for supporting the light receiving element 35 may be provided in a space surrounded by the reflecting surface 32a such that the focal point of the reflecting surface 32a is arranged on the surface of the light receiving element 35 with such a shape.

As used herein, the following directional terms "front, back, above, downward, right, left, vertical, horizontal, below, transverse, row and column" as well as any other similar directional terms refer to those instructions of a device equipped with the present invention. Accordingly, these terms, as utilized to describe the present invention should be interpreted relative to a device equipped with the present invention.

The term "configured" is used to describe a component, unit or part of a device includes hardware and/or software that is constructed and/or programmed to carry out the desired function.

Moreover, terms that are expressed as "means-plus-function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While various embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A measuring device comprising:
   an irradiator that irradiates electromagnetic waves to an inspection object;
   a light collector having a reflecting surface that guides, to a light-collecting surface, electromagnetic waves whose incident angle with respect to an incident end facing the inspection object is within a predetermined angle, among the electromagnetic waves that have been transmitted through the inspection object;
   a detector comprising a light receiving sensor that detects the electromagnetic waves guided to the light-collecting surface;
   a processor that receives signals outputted from the detector and measures a characteristic of the inspection object based on the signals; and
   an inner-surface reflecting mirror that is polygonal and disposed between the irradiator and the inspection object,
   wherein a radius of an exit end of the light collector is equal to or less than a radius of a surface of the light receiving sensor, and
   wherein a length of a diagonal line that connects two opposite corners of the inner-surface reflecting mirror is equal to or smaller than a diameter of the incident end of the light collector.

2. The measuring device according to claim 1, wherein the light-collecting surface is an opening surface in an exit end facing the detector.

3. The measuring device according to claim 1, wherein the reflecting surface is a compound paraboloidal surface.

4. The measuring device according to claim 1, wherein an opening area of the incident end of the light collector is larger than an irradiation area where the inspection object is irradiated with the electromagnetic waves.

5. The measuring device according to claim 1, wherein the inspection object has a sheet-like shape.

6. The measuring device according to claim 1, wherein
   the electromagnetic waves are infrared, visible, or ultraviolet rays including a plurality of wavelength components, and
   the characteristic is an amount or proportion of liquid contained in the inspection object.

7. The measuring device according to claim 6, wherein the electromagnetic waves include:
   a first wavelength component at which an absorptivity of the liquid contained in the inspection object is higher than an absorptivity of a main component of the inspection object;
   a second wavelength component at which an absorptivity of the main component is higher than an absorptivity of the liquid; and
   a third wavelength component at which an absorptivity of the liquid is lower than that of the first wavelength component and an absorptivity of the main component is lower than that of the second wavelength component.

8. The measuring device according to claim 2, wherein
the incident end and the exit end of the light collector are
shaped as concentric circles, and
wherein a radius of the incident end of the light collector
is greater than a radius of the exit end of the light
collector.

9. The measuring device according to claim 8, wherein
$L=(d1+d2) \cot \theta$, where:
d1 is the radius of the exit end of the light collector,
d2 is the radius of the incident end of the light collector,
θ is an angle that allows the electromagnetic waves
reflected from the reflecting surface to be emitted from
the exit end, and
L is a thickness of the light collector.

10. The measuring device according to claim 9, wherein
the light receiving sensor is disposed at a position where
the light receiving surface of the light receiving sensor
is perpendicular to an optical axis of the electromagnetic waves and a center of the light receiving sensor is
on an extension line of the optical axis.

11. The measuring device according to claim 10, wherein
the light receiving sensor is any one of:
a photoconductive element containing lead sulfide as a
main component,
a photoconductive element containing germanium as a
main component, and
a ternary mixed crystal semiconductor element containing
indium, gallium, and arsenic as main components.

12. The measuring device according to claim 1, wherein
the inner-surface reflecting mirror reflects the electromagnetic waves emitted from the irradiator multiple times
and achieves uniform intensity distribution.

13. The measuring device according to claim 12, further
comprising:
an upper sensor head comprising the irradiator and the
inner-surface reflecting mirror; and
a lower sensor head comprising the light collector and the
detector.

14. The measuring device according to claim 13, wherein
driving of the upper sensor head and the lower sensor head
starts at the same time as driving of the irradiator.

15. The measuring device according to claim 7, wherein
the irradiator comprises:
a first light emitting element that emits the electromagnetic waves of the first wavelength component;
a second light emitting element that emits the electromagnetic waves of the second wavelength component;
and
a third light emitting element that emits the electromagnetic waves of the third wavelength component.

16. The measuring device according to claim 15, wherein
each of the first light emitting element, the second light
emitting element, and the third light emitting element emits
the electromagnetic waves with their intensities modulated
at different frequencies.

17. The measuring device according to claim 15, wherein
the inspection object is paper whose the main component
is cellulose,
the first light emitting element emits the electromagnetic
waves of the first wavelength component at which an
absorptivity of water contained in the paper is higher
than an absorptivity of the cellulose,
the second light emitting element emits the electromagnetic waves of the second wavelength component at
which an absorptivity of the cellulose is higher than an
absorptivity of the water, and
the third light emitting element emits the electromagnetic
waves of the third wavelength component at which an
absorptivity of the water is lower than that of the first
wavelength component and an absorptivity of the cellulose is lower than that of the second wavelength
component.

* * * * *